(12) United States Patent
Liu et al.

(10) Patent No.: US 9,427,471 B2
(45) Date of Patent: Aug. 30, 2016

(54) METHOD AND IMPROVED PHARMACEUTICAL COMPOSITION FOR ENHANCING TRANSDERMAL DELIVERY OF PDE-5 INHIBITOR

(75) Inventors: Yee-Chien Liu, New Taipei (TW); Pei-Ling Wu, New Taipei (TW)

(73) Assignee: Tritech Biopharmaceuticals Co., Ltd., New Taipei (TW)

( * ) Notice: Subject to any disclaimer, the term of this patent is extended or adjusted under 35 U.S.C. 154(b) by 0 days.

(21) Appl. No.: 14/364,000

(22) PCT Filed: Dec. 26, 2011

(86) PCT No.: PCT/CN2011/084647
§ 371 (c)(1),
(2), (4) Date: Sep. 24, 2014

(87) PCT Pub. No.: WO2013/097074
PCT Pub. Date: Jul. 4, 2013

(65) Prior Publication Data
US 2015/0057284 A1     Feb. 26, 2015

(51) Int. Cl.
| C07D 487/00 | (2006.01) |
| A61K 31/53 | (2006.01) |
| A61K 47/22 | (2006.01) |
| A61K 31/519 | (2006.01) |
| A61K 9/00 | (2006.01) |
| A61K 47/10 | (2006.01) |
| A61K 47/18 | (2006.01) |
| A61K 9/06 | (2006.01) |
| A61K 9/70 | (2006.01) |

(52) U.S. Cl.
CPC .............. *A61K 47/22* (2013.01); *A61K 9/0014* (2013.01); *A61K 9/06* (2013.01); *A61K 9/7023* (2013.01); *A61K 31/519* (2013.01); *A61K 31/53* (2013.01); *A61K 47/10* (2013.01); *A61K 47/186* (2013.01)

(58) Field of Classification Search
USPC .......................................... 544/184; 514/243
See application file for complete search history.

(56) References Cited

U.S. PATENT DOCUMENTS

| 4,450,090 A | * | 5/1984 | Kinney | ................. | A61K 8/466 |
| | | | | | 510/124 |
| 2003/0069317 A1 | * | 4/2003 | Seitz, Jr. | ................ | A01N 31/08 |
| | | | | | 514/731 |
| 2005/0271596 A1 | * | 12/2005 | Friedman | ............... | A61K 8/046 |
| | | | | | 424/45 |
| 2010/0008991 A1 | | 1/2010 | Mantelle et al. | | |

FOREIGN PATENT DOCUMENTS

EP     0992240 A1     4/2000

* cited by examiner

*Primary Examiner* — Paul Zarek
*Assistant Examiner* — George W Kosturko
(74) *Attorney, Agent, or Firm* — Muncy, Geissler, Olds & Lowe, P.C.

(57) ABSTRACT

The present disclosure relates to the use of an agent that enhances transdermal delivery of a PDE-5 inhibitor. More particularly, the present disclosure provides improved method and composition that promotes transdermal delivery of a PDE-5 inhibitor for the treatment of the PDE-5 mediated conditions and/or diseases.

8 Claims, 2 Drawing Sheets

METHOD AND IMPROVED PHARMACEUTICAL COMPOSITION FOR ENHANCING TRANSDERMAL DELIVERY OF PDE-5 INHIBITOR

BACKGROUND OF THE INVENTION

1. Field of the Invention

The present disclosure relates to the field of drug delivery, and more particularly to the use of an enhancer to enhance the permeation of a pharmacologically active agent through human or animal skin.

2. Description of Related Art

Phosphodiesterase (PDE) is an enzyme found in various tissues. The interest in PDEs as molecular targets of drug action has grown with the development of isozyme-selective PDE inhibitors that offer potent inhibition of selected isozymes without the side-effects attributed to nonselective inhibitors. Sildenafil, vardenafil and tadalafil are inhibitors of cGMP-specific phosphodiesterase type 5 (PDE-5).

PDE-5 inhibitors are used to treat primary pulmonary hypertension (PPH), which is a disease in which blood vessels in the lungs become abnormally narrow; and erectile dysfunction. There are now three oral formulation containing PDE-5 inhibitors for treating erectile dysfunction (ED), they are Viagra (containing sildenafil) by Pfizer, Levitra (containing vardenafil) by Bayer Pharmaceutical and Glaxo-Smith-Kline-Beecham/Schering Plough, and Cialis (containing tadalafil) by Lilly-ICOS.

Although oral delivery is a convenient and non-invasive way of delivering a pharmacologically active compound, yet it has its own disadvantages. For example, it is slow acting, for the drug would have to go through the gastrointestinal system of the recipient before it can reach the intended target site such as penis for ED treatment. Further, it is more likely to cause a number of side-effects, for the drug will be circulated systematically instead of exerting its function locally.

Transdermal delivery is a feasible solution to the above-identified disadvantages of oral formulation of PDE-5 inhibitors. Various substances are known to enhance the ability of drugs and agents to diffuse through the skin and other tissues. The more popular approach has been the employment of surface active agents. However, many surface active agents enhance the permeability by actually damaging the barrier tissue. Only slight to moderate enhancement of penetration is effected with the prior art surface active agents. Another approach is to use certain organic solvents, such as dimethylsulfoxide (DMSO), dimethyl formamide (DMF) or N,N-dimethylacetamide, to enhance the penetration of active substances through stratum corneum. A disadvantage of using these solvents is that they are systemically distributed in a short period of time and cause undesirable side effects.

Thus, it would be desirable to provide an improved transdermal formulation that overcomes the above-identified deficiency. Accordingly, this invention identifies several compounds that may enhance transdermal delivery of PDE-5 inhibitors, hence are useful for the development of an improved medicament for treating conditions or diseases mediated by PDE-5.

SUMMARY

The present disclosure is based on the finding that certain agent(s) is effective as an enhancer to promote transdermal delivery of a PDE-5 inhibitor, hence is useful as an agent or an adjuvant for developing a topical medicament for treating conditions or diseases mediated by PDE-5 such as erectile dysfunction or primary pulmonary hypertension.

Accordingly, it is therefore an object of the present disclosure to provide an improved transdermal pharmaceutical composition with an enhanced transdermal absorption rate of a PDE-5 inhibitor. According to embodiments of the present disclosure, the improved composition includes a phosphodiesterase type-5 (PDE-5) inhibitor or a pharmaceutically acceptable salt thereof, and a pharmaceutically acceptable excipient; and the improvement of the composition lies in having an enhancer of this invention, wherein the PDE-5 inhibitor and the enhancer are present in a ratio from about 20:1 to 2:1 in the improved composition of this invention. In one preferred example, the PDE-5 and the enhancer are present in a ratio of about 5:1 in the improved transdermal pharmaceutical composition.

According to embodiments of the present disclosure, the enhancer is selected from the group consisting of cocamidopropyl betaine, sodium lauroamphoacetate, quaternium-60, isostearamidopropyl morpholine lactate, dipropylene glycol and a combination thereof. In one example, the enhancer is cocamidopropyl betaine. In another example, the enhancer is a mixture of cocamidopropyl betaine and sodium lauroamphoacetate. In still another example, the enhancer is a mixture of cocamidopropyl betaine, sodium lauroamphoacetate, and quaternium-60. In one preferred example, the enhancer is a mixture of cocamidopropyl betaine, sodium lauroamphoacetate, quaternium-60, isostearamidopropyl morpholine lactate, and dipropylene glycol. The PDE-5 inhibitor is any of sildenafil, tadalafi or vardenafil. In one preferred example, the PDE-5 inhibitor is vardenafil, which is not in crystalline state.

According to embodiments of the present disclosure, the improved pharmaceutical composition may be formulated into the form of a solution, a paste, a lotion, a cream, a gel, or a patch. In one embodiment, improved pharmaceutical composition is a gel. In another embodiment, the improved pharmaceutical composition is a skin patch.

In another aspect, the present disclosure provides a method for enhancing transdermal delivery of a PDE-5 inhibitor in a subject. According to embodiments of the present disclosure, the method includes steps of administering to the subject the improved pharmaceutical composition of the present disclosure, which includes a PDE-5 inhibitor or a pharmaceutically acceptable salt thereof, a pharmaceutically acceptable excipient, and an enhancer of the present invention; wherein the PDE-5 inhibitor and the enhancer are present in a ratio from about 20:1 to 2:1 in the improved composition. In one preferred example, the PDE-5 and the enhancer are administered in a ratio of about 5:1.

According to embodiments of the present disclosure, the enhancer of the present invention is any of cocamidopropyl betaine, sodium lauroamphoacetate, quaternium-60, isostearamidopropyl morpholine lactate, dipropylene glycol or a combination thereof. In one example, the enhancer is cocamidopropyl betaine. In another example, the enhancer is a mixture of cocamidopropyl betaine and sodium lauroamphoacetate. In still another example, the enhancer is a mixture of cocamidopropyl betaine, sodium lauroamphoacetate and quaternium-60. In one preferred example, the enhancer is a mixture of cocamidopropyl betaine, sodium lauroamphoacetate, quaternium-60, isostearamidopropyl morpholine lactate, and dipropylene glycol. The PDE-5 inhibitor is any of sildenafil, tadalafi or vardenafil. In one preferred example, the PDE-5 inhibitor is vardenafil, which is not in crystalline state.

The improved method and/or pharmaceutical composition of the present disclosure can attain the same therapeutic benefits to the recipient thereof at a reduced level of PDE-5 inhibitor.

BRIEF DESCRIPTION OF THE DRAWINGS

These and other features, aspects and advantages of the present invention will become better understood with reference to the following description, appended claims and the accompanying drawings, where:

DESCRIPTION

Figure 1:
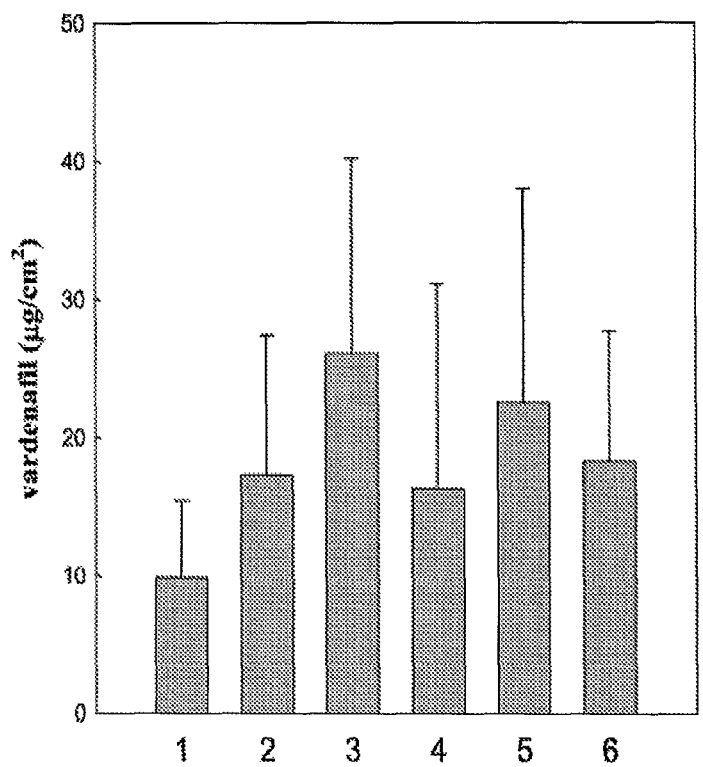
FIG. 1 illustrates the effects of formulations of Example 2.1 on in vitro transdermal delivery of vardenafil in accordance with one embodiment of the present disclosure.

These and other features, aspects and advantages of the present invention will become better understood with reference to the following description and the appended claims The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

DEFINITIONS

For convenience, certain terms employed in the specification, examples and appended claims are collected here. Unless defined otherwise, all technical and scientific terms used herein have the same meaning as commonly understood by one of the ordinary skill in the art to which this invention belongs.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "enhancer" is defined as a substance that, when added to the pharmaceutical composition, enhances the absorption kinetics, hence the bioavailability of a pharmacologically active agent, i.e., the PDE-5 inhibitor, while having few or none of direct therapeutically effects when given by itself.

The term "transdermal delivery" as used herein refers to delivery by passage of a compound or drug through the skin and into the bloodstream.

"Enhanced delivery", "enhanced permeability", "enhanced permeation", or "enhanced absorption" are used interchangeably herein to represent an increase in the permeability of skin to a pharmacologically active agent, i.e., so as to increase the rate at which the drug (e.g., the PDE-5 inhibitor) permeates through the skin and enters the bloodstream. The enhanced permeation effected through the use of the improved composition of the present invention can be observed by measuring the rate of diffusion of a drug through animal or human skin using a diffusion cell apparatus as described in the Examples herein.

As used herein, a "pharmaceutically acceptable" component is one that is suitable for use with humans and/or animals without undue adverse side effects (such as toxicity, irritation, and allergic response) commensurate with a reasonable benefit/risk ratio.

The term "an effective amount" as used herein refers to an amount effective, at dosages, and for periods of time necessary, to achieve the desired therapeutically desired results with respect to the treatment of diseases or conditions mediated by PDE-5, such as erectile dysfunction or primary pulmonary hypertension. It will be appreciated that the therapeutically effective amount of the PDE-5 inhibitor will vary from subject to subject not only for the particular PDE-5 inhibitor selected, the route of administration, and the ability of the PDE-5 inhibitor (alone or in combination with one or more PDE-5 inhibitor or other drugs) to elicit a desired response in the subject, but also factors such as state or severity of the condition to be alleviated, age, weight of the subject, the state of being of the subject, and the severity of the condition being treated, concurrent medication or special diets then being followed by the subject, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the compound or composition are outweighed by the therapeutically beneficial effects. Preferably, the PDE-5 inhibitor is administered at a dosage and for a time such that the severity of the symptoms is decreased.

The term "subject" refers to any animal (e.g., a mammal), including, but are not limited to humans, non-human primates, which is to be subjected under the treatment of this invention. Typically, "patient" and "subject" are used interchangeably herein in reference to a human subject.

The term "excipient" as used herein means any inert substance (such as a powder or liquid) that forms a vehicle/carrier for the PDE-5 inhibitor and/or enhancer. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

The practices of this invention are hereinafter described in detail with respect to a method and a pharmaceutical composition that improves the transdermal delivery effects, and, thus, enhances the bioavailability of a PDE-5 inhibitor in a subject.

According to embodiments of the present disclosure, the improved transdermal pharmaceutical composition comprises, a phosphodiesterase type-5 (PDE-5) inhibitor or a pharmaceutically acceptable salt thereof, and a pharmaceutically acceptable excipient, wherein the improvement comprises, an enhancer selected from the group consisting of cocamidopropyl betaine, sodium lauroamphoacetate, quaternium-60, isostearamidopropyl morpholine lactate, dipropylene glycol and a combination thereof; wherein the PDE-5 inhibitor and the enhancer are present in a ratio from about 20:1 to 2:1 in the improved transdermal pharmaceutical composition The PDE-5 inhibitors suitable for use in this invention are those known in the art, which include, but are not limited to, sildenafil, tadalafi and vardenafil. In one preferred example, the PDE-5 inhibitor is vardenafil.

The enhancer suitable for use in this invention includes, but is not limited to, cocamidopropyl betaine, sodium lauroamphoacetate, quaternium-60, isostearamidopropyl morpholine lactate, dipropylene glycol and a combination thereof. Cocamidopropyl betaine or {[3-(Dodecanoylamino)propyl](dimethyl)ammonio}acetate is a synthetic surfactant derived from coconut oil and dimethylaminopropylamine. Sodium lauroamphoacetate or Sodium 2-[1-(2-hydroxyethyl)-2-undecyl-4,5-dihydroimidazol-1-ium-1-yl]acetate is an amphoacetate commonly used in moisturizers. Quaternium-60 is an active quaternary commonly dissolved in propylene glycol. By including the enhancer in the present improved composition, it is ensured that the PDE-5 inhibitor is completely dissolved in, or without being crystallized out of, the improved composition, and thereby increases the availability of PDE-5 inhibitor for transporting across stratum corneum.

According to embodiments of the present disclosure, the PDE-5 inhibitor and the enhancer are present in a ratio from about 20:1 to 2:1, preferably about 5:1 in the improved composition. Specifically, the PDE-sand the enhancer are present in the improved composition in a ratio of about 20:1, 19:1, 18:1, 17:1, 16:1, 15:1, 14:1, 13:1, 12:1, 11:1, 10:1, 9:1, 8:1, 7:1, 6:1, 5:1. 4:1, 3:1 or 2:1. In one example, the PDE-5 inhibitor is vardenafil, and the enhancer is cocamidopropyl betaine; and the PDE-5 inhibitor and the enhancer are present in a ratio of about 5:1 in the improved composition. In another example, the PDE-5 inhibitor is vardenafil, and the enhancer is a one-to-one mixture of cocamidopropyl betaine and sodium lauroamphoacetate; and the PDE-5 inhibitor and the enhancer are present in a ratio of about 6:1 in the improved composition. In still another example, the PDE-5 inhibitor is vardenafil, and the enhancer is a mixture of cocamidopropyl betaine, sodium lauroamphoacetate and quaternium-60; and the PDE-5 inhibitor and the enhancer are present in a ratio of about 4:1 in the improved composition. In a further example, the PDE-5 inhibitor is vardenafil, and the enhancer is a mixture of cocamidopropyl betaine, sodium lauroamphoacetate, quaternium-60, isostearamidopropyl morpholine lactate, and dipropylene glycol; and the PDE-5 inhibitor and the enhancer are present in a ratio of about 3:1 in the improved composition.

The pharmaceutical compositions of this invention may be formulated into a variety of dosage forms for topical application. A wide variety of dermatologically acceptable inert excipients well known to the art may be employed. The topical compositions may include liquids, pastes, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

When formulated for presentation as a solution, the improved composition can include volatile carriers such as ethanol and water as well as non-volatile carriers such as medium chain length triglyceride and straight chain aliphatic alcohols. Thus a typical solution composition of this invention includes at least, a concentration of the PDE-5 inhibitor in a range of about 1-20% by weight, a concentration of the enhancer in a range of about 0.2-5% by weight, and a concentration of volatile and non-volatile carriers in the range of about 0.5-98% by weight, respectively.

When formulated for presentation as a lotion, the improved composition can include a finely divided solid and a thickener. Thus a typical lotion composition of this invention includes at least, a concentration of the PDE-5 inhibitor in a range of about 1-20% by weight, a concentration of the enhancer in a range of about 0.2-5% by weight, a concentration of the finely divided solid in the range of about 0.5-5% by weight, and a concentration of the thickener in the range of about 2-5% by weight.

When formulated for presentation as a cream, the improved composition can include emollient and an emulsifier, as well as an antioxidant and/or preservative. Thus a typical cream composition of this invention includes at least, a concentration of the PDE-5 inhibitor in a range of about 1-20% by weight, a concentration of the enhancer in a range of about 0.2-5% by weight, a concentration of the emollient in the range of about 0-50% by weight, and a concentration of the emulsifier in the range of about 0-20% by weight.

When formulated for presentation as a gel, the improved composition can include a gelling agent such as a finely divided solid and/or thickener in concentrations that produce a loose molecular network inhibiting the free movement of liquid ingredients. Thus a typical gel composition of this invention includes at least, a concentration of the PDE-5 inhibitor in a range of about 1-20% by weight, a concentration of the enhancer in a range of about 0.2-5% by weight, a concentration of the thickener in the range of about 2-5% by weigh, and a concentration of the finely divided solid in the range of about 0-20% by weight.

The improved compositions of this invention may also be formulated into an aerosol formulation for drug delivery through skin. Thus a typical aerosol composition of this invention includes, at least, a concentration of the PDE-5 inhibitor in a range of about 1-20% by weight, a concentration of the enhancer in a range of about 0.2-5% by weight, a concentration of a propellant and/or co-solvent in a range of 10-90% by weight. Suitable propellants and/or co-solvents for solubilizing the PDE-5 inhibitor and the enhancer of this invention in medicinal aerosol formulations are well known in this art. Typical propellants are hydrofluoroalkanes such as 1,1,1,2-tetrafluoroethane (HFA-134a), 1,1,1,2,3,3,3-heptafluoropropane (HFA-227ea). pentafluoroethane (HFA-125), 1,1-difluoroethane (HFA-152a), difluoromethane (HFA-32) and the like. Typical co-solvents include, but not limited to, alcohols, polyols, alkoxy derivatives, fatty acid alkyl esters, polyalkylene glycols, dimethylsulphoxide and the like.

In a particularly preferred embodiment, the improved composition is administered to the recipient by means of a skin patch. The skin patch is prepared by incorporating in a matrix such as a gauze pad the improved formulation of this invention (e.g., any of the gel formulations 2 to 5 of Example 2.1). Transdermal delivery is accomplished by exposing the recipient's skin to one side of the patch for an extended period of time, so that PDE-5 inhibitor is released on to and across the recipient's skin. Many suitable transdermal delivery patches are known, ranging from a simple gauze pad impregnated with the formulation of this invention and secured to the skin with an adhesive bandage to multilayer structures. Typically, a transdermal delivery patch may also contain other added substances that enhance the penetration of the PDE-5 inhibitor, i.e., substances other than the enhancer identified by the inventors of this application. Many known enhancers may be used together with the enhancers of this invention, to improve skin penetration of PDE-5 inhibitor.

The improved composition of this invention can be prepared by conventional procedures, such as those described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable. To minimize contamination from the growth of microorganisms, sterilized equipment is preferably used. Once blended, the composition can be packaged and stored in any suitable container inert to the contents including aluminum, glass, stainless steel, and solvent resistant plastics including polyamide, polyester, polypropylene, and ABS polymer. Storage is preferably in a cool place away from strong sunlight. Continued sterility can be assured by conventional techniques including aseptic packaging and post-sterilization in the final package by electron beam exposure.

Accordingly, this invention also provides methods of treating mammals, preferably humans, for conditions or diseases mediated by PDE-5, such as erectile dysfunction or primary pulmonary hypertension. The method comprises the step of administrating the improved pharmaceutical composition of this invention to the mammals in need thereof. Accordingly, such composition is transdermally administered to a mammal, preferably human, with an enhanced absorption of the PDE-5 inhibitor by the human subject.

The present invention will now be described more specifically with reference to the following embodiments, which are provided for the purpose of demonstration rather than limitation.

EXAMPLES

Example 1

In Vitro Permeation Analysis

The permeation test was carried out using in vitro Franz diffusion cell with a diffusion area of 0.785 cm$^2$. A piece of rat (Sprague-Dawley) skin tissue was mounted between the two half-cells and fastened with a clamp. Aliquots of 1% (wt %) vardenafil with or without the addition of the enhancer of this disclosure, such as 0.3% (wt %) cocamidopropyl betaine, 1% (wt %) sodium lauroamphoacetate, 1% (wt %) isostearamidopropyl morpholine lactate, 1% (wt %) quaternium-60 or dipropyl glycol, were applied to the Donor compartment to start the experiment. The receiver compartment was filled with PBS and the temperature was held at 37° C. Samples were taken at certain time intervals and assayed by HPLC. Amounts of vardenafil accumulated in the receiver compartment were calculated and results were summarized in FIG. 1.

As depicted in FIG. 1, an increase in skin permeation was achieved with the inclusion of the enhancer in the formulation; penetration effect of the enhancer was seen with the amount of vardenafil in the receiving side of Franz Diffusion chamber increased by about 0.5-2 folds as compared with that of the control (i.e., 1% vardenafil).

Example 2

In Vivo Permeation Analysis 2.1 Preparation of Gels Containing Vardenafil

Formulations (#1 to 4) were prepared by stirring together separately prepared pre-mixtures of water insoluble ingredients and the water-soluble ingredients as tabulated bellow (all quantities are in weight %) until gels were formed, then adjusted the pH of the respective gel formulations to a range between 2.5 and 3.5.

| Formulation # | 1 | 2 | 3 | 4 |
|---|---|---|---|---|
| Water-insoluble | | | | |
| Methyl paraben | 0.2 | 0.2 | 0.2 | 0.2 |
| Propyl paraben | 0.2 | 0.2 | 0.2 | 0.2 |
| Propylene glycol | 5 | 5 | 5 | 5 |
| Ethanol | 5 | 5 | 5 | 5 |
| cellulose | 0.5 | 0.5 | 0.5 | 0.5 |
| Water-soluble | | | | |
| L-arginine | 0.5 | 0.5 | 0.5 | 0.5 |
| EDTA | 0.5 | 0.5 | 0.5 | 0.5 |
| NaCl | — | 0.5 | 0.5 | 0.5 |
| Vardenafil HCl | 3 | 5 | 7 | 6 |
| Tartaric acid | — | 0.3 | 0.3 | 0.3 |
| Cocamidopropyl betaine | — | 0.3 | 0.15 | 0.15 |
| Sodium lauroamphoacetate | — | — | 1 | 0.5 |
| Quaternium-60 | — | — | — | 1 |
| H$_2$O | 85.1 | 82 | 79.15 | 79.65 |

2.2 Preparation of Skin Patch Containing Vardenafil

Formulation (#5) was prepared using ingredients tabulated bellowed (all ingredients were listed in weight %) in accordance with similar procedure as described above in example 2.1. The thus obtained formulation (#5) was then applied onto the surface of a non-woven cloth, and let stand for 7 days until it gelled, thereby forming the desired skin patch.

| Formulation # | 5 |
|---|---|
| Water-insoluble | |
| Methyl paraben | 0.2 |
| Propyl paraben | 0.2 |
| Propylene glycol | 10 |

-continued

| Formulation # | 5 |
|---|---|
| Ethanol | 10 |
| Sodium polyacrylate | 5 |
| Polyacrlic acid | 2 |
| cellulose | 1 |
| Water-soluble | |
| L-arginine | 1 |
| EDTA | 0.3 |
| NaCl | 1 |
| Vardenafil HCl | 8 |
| Tartaric acid | 0.2 |
| Cocamidopropyl betaine | 0.2 |
| Sodium lauroamphoacetate | 0.3 |
| Quaternium-60 | 0.5 |
| Isostearamidopropyl morpholine lactate | 1 |
| Dipropylene glycol | 0.5 |
| $H_2O$ | 58.6 |

2.3 In Vivo Permeation Analysis

In vivo skin permeation tests were carried out using the gel formulations of example 2.1 and the skin patch of example 2.2. Briefly, small aliquots (about 0.5 ml) of gel formulations #1 to 4 or a small piece of the skin patch (3 cm×5 cm×0.15 cm) was applied to the left ear of a rabbit, after certain period of time, 1 ml of blood was drawn from the rabbit's right ear artery and analyzed for the amount of vardenafil. Specifically, the blood was drawn after 1 hour when gel formulation was used; and 6 hours when skin patch was applied. Results are illustrated in FIG. 2.

Figure 2:
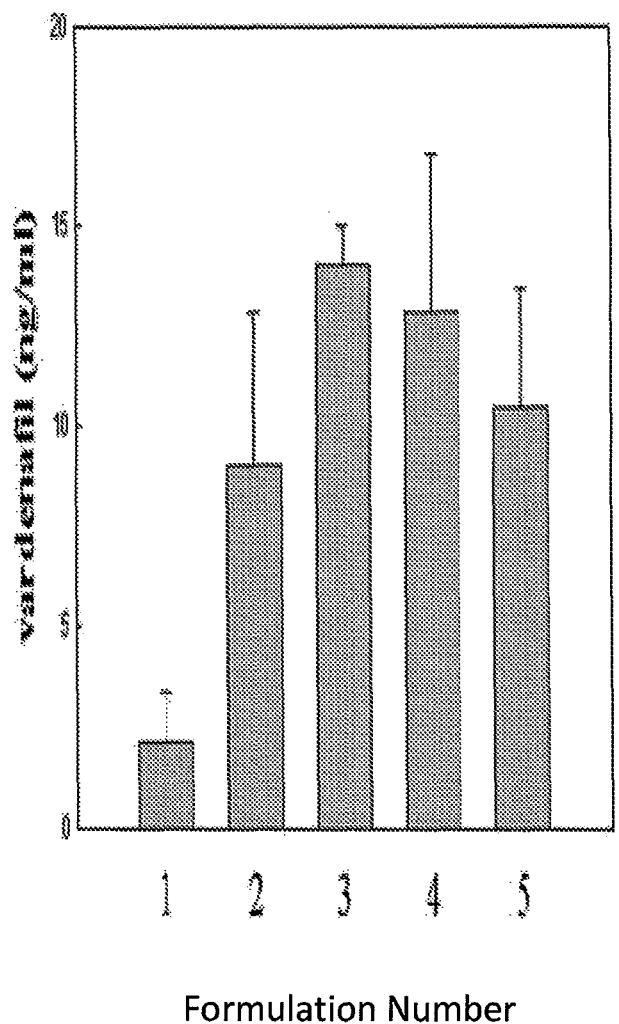
FIG. 2 illustrates the effects of the formulations of Example 2.1 and the skin patch of Example 2.2 on in vivo transdermal delivery of vardenafil in accordance with one embodiment of the present disclosure.

It is evident from the results depicted in FIG. 2, the enhancer(s) identified in the present invention, when applied simultaneously with vardenafil, either alone or in combination, significantly enhances the permeation of vardenafil across the skin, with the amount of vardenafil found in the blood stream increased by about 4 to 5 folds, as compared with that of the control.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

The invention claimed is:

1. A transdermal pharmaceutical composition comprising an effective amount of vardenafil or a pharmaceutically acceptable salt thereof; and an enhancer consists of cocamidopropyl betaine, sodium lauroamphoacetate, quaternium-60, isostearamidopropyl morpholine lactate, and dipropylene glycol; wherein vardenafil and the enhancer are present in a ratio from about 20:1 to 2:1 by weight in the transdermal pharmaceutical composition, and the transdermal pharmaceutical composition is in the form of a solution, a gel or a patch; and a pharmaceutically acceptable excipient.

2. The transdermal pharmaceutical composition of claim 1, wherein vardenafil and the enhancer are present in the transdermal pharmaceutical composition in a ratio of about 10:1.

3. The transdermal pharmaceutical composition of claim 1, wherein vardenafil is not in a crystalline state.

4. A method for enhancing transdermal delivery of vardenafil in a subject comprising administering to the subject vardenafil and an enhancer in a ratio of about 20:1 to 2:1 by weight, wherein the enhancer consists of cocamidopropyl betaine, sodium lauroamphoacetate, quaternium-60, isostearamidopropyl morpholine lactate, and dipropylene glycol.

5. The method of claim 4, wherein vardenafil and the enhancer are administered in a ratio of about 10:1 by weight.

6. The method of claim 4, wherein vardenafil is not in a crystalline state.

7. The transdermal pharmaceutical composition of claim 1, wherein vardenafil and the enhancer are present in the transdermal pharmaceutical composition in a ratio of about 3:1 by weight.

8. The method of claim 4, wherein vardenafil and the enhancer are administered in a ratio of about 3:1 by weight.

* * * * *